US00PP12607P2

(12) United States Plant Patent
van Rijn

(10) Patent No.: US PP12,607 P2
(45) Date of Patent: May 7, 2002

(54) ANTHURIUM PLANT NAMED 'WENDY'

(75) Inventor: Leonardus van Rijn, Schipluiden (NL)

(73) Assignee: Rijnplant, Schipluiden (NL)

( * ) Notice: Subject to any disclaimer, the term of this patent is extended or adjusted under 35 U.S.C. 154(b) by 0 days.

(21) Appl. No.: 09/563,940

(22) Filed: May 4, 2000

(51) Int. Cl.[7] ..... A01H 5/00

(52) U.S. Cl. ..... Plt./367

(58) Field of Search ..... Plt./367

(56) References Cited

PUBLICATIONS

UPOV ROM GTITM Computer database, GTI JOUVE Retrieval software, citation for 'Wendy'.*

* cited by examiner

*Primary Examiner*—Bruce R. Campell
*Assistant Examiner*—Wendy A Baker
(74) *Attorney, Agent, or Firm*—C. A. Whealy

(57) ABSTRACT

A distinct cultivar of Anthurium plant named 'Wendy', characterized by its upright and somewhat outwardly spreading plant habit; freely clumping growth habit; durable dark green leaves; strong root system; numerous light pink-colored spathes that are positioned upright and beyond the foliage on strong and erect scapes; and good post-production longevity.

2 Drawing Sheets

BACKGROUND OF THE INVENTION

The present invention relates to a new and distinct cultivar of Anthurium plant, botanically known as *Anthurium andreanum,* and hereinafter referred to by the cultivar name Wendy.

The new Anthurium is a product of a planned breeding program conducted by the Inventor in Schipluiden, The Netherlands. The objective of the program is to create and develop new Anthurium cultivars that have a freely clumping growth habit, durable leaves and spathes, strong roots, attractive spathe color, and good post-production longevity.

The new Anthurium originated from a cross by the Inventor in June, 1995 of the Inventor's proprietary *Anthurium andreanum* selection code number 93-2 as the female, or seed, parent with the Inventor's proprietary *Anthurium andreanum* selection code number 93-20 as the male, or pollen, parent. The cultivar Wendy was discovered and selected by the Inventor as a plant within the progeny of the stated cross in a controlled environment in Schipluiden, The Netherlands in February, 1997.

Asexual propagation of the new cultivar by tissue cultivar of meristem tips in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Wendy. These characteristics in combination distinguish 'Wendy' as a new and distinct cultivar:

1. Upright and somewhat outwardly spreading plant habit.
2. Freely clumping growth habit.

3. Durable dark green leaves.
4. Strong root system.
5. Numerous light pink-colored spathes that are positioned upright and beyond the foliage on strong and erect scapes.
6. Good post-production longevity.

The new Anthurium can be compared to the female parent, the Inventor's proprietary selection code number 93-2. In side-by-side comparisons conducted in Schipluiden, The Netherlands, plants of the new Anthurium differ from plants of selection code number 93-2 in the following characteristics:

1. Plants of the new Anthurium are more freely clumping than plants of the selection code number 93-2.
2. Plants of the new Anthurium have thinner and more rounded leaves than plants of the selection code number 93-2.
3. Plants of the new Anthurium have larger and more rounded spathes than plants of the selection code number 93-2.
4. Plants of the new Anthurium have longer lasting spathes than plants of the selection code number 93-2.

The new Anthurium can be compared to the male parent, the Inventor's proprietary selection code number 93-20. In side-by-side comparisons conducted in Schipluiden, The Netherlands, plants of the new Anthurium differ from plants of selection code number 93-20 in the following characteristics:

1. Plants of the new Anthurium have larger and thicker leaves as plants of the selection code number 93-20.
2. Plants of the new Anthurium have thicker but smaller spathes than plants of the selection code number 93-20.
3. Plants of the new Anthurium have light pink-colored spathes whereas plants of the selection code number 93-20 have red-colored spathes.

The new Anthurium can be compared to the Anthurium cultivar Goliath, not patented. In side-by-side comparisons conducted in Schipluiden, The Netherlands, plants of the new Anthurium differ from plants of the cultivar Goliath in the following characteristics:

1. Plants of the new Anthurium are faster growing than plants of the cultivar Goliath.
2. Plants of the new Anthurium have larger, more rounded and thicker leaves than plants of the cultivar Goliath.
3. Plants of the new Anthurium have longer petioles than plants of the cultivar Goliath.
4. Plants of the new Anthurium and plants of the cultivar Goliath differ in spathe color.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which more accurately describe the actual colors of the new Anthurium.

The photograph at the top of the first sheet comprises a top perspective view of a typical potted plant of the cultivar Wendy.

The photograph at the bottom of the first sheet comprises a close-up view of an immature spathe and spadix.

The photograph on the second sheet comprises a close-up view of a typical leaf and mature spathes and spadices of the cultivar Wendy.

DETAILED BOTANICAL DESCRIPTION

In the following description, color references are made to The Royal Horticultural Society Colour Chart except where general terms of ordinary dictionary significance are used. The following observations and measurements describe 40-week old plants grown in 17-cm containers in Schipluiden, The Netherlands, in a glass greenhouse with an average day temperature of 25° C. and an average night temperature of 19° C.

Botanical classification: *Anthurium andreanum* cultivar Wendy.

Parentage:

*Female parent.*—Inventor's proprietary *Anthurium andreanum* selection code number 93-2, not patented.

*Male parent.*—Inventor's proprietary *Anthurium andreanum* selection code number 93-20, not patented.

Propagation:

*Method.*—Typically by tissue culture of meristem tips.

*Time to initiate roots.*—About 70 or 84 days at 24° C. or 21° C., respectively.

*Root description.*—Numerous and very strong fleshy roots.

Plant description:

*Plant shape.*—Upright and somewhat outwardly spreading, inverted triangle, symmetrical.

*Growth habit.*—Freely clumping, bushy and dense. Appropriate for 17 to 35-cm containers.

*Plant height.*—About 56 cm.

*Plant diameter.*—About 75 cm.

*Plant vigor.*—High.

*Growth rate.*—Moderate to rapid.

*Crop time.*—About 10 months are usually required from planting of young plants to finished plants in a 17-cm container.

*Foliage description.*—Quantity per plant: About 30 to 40. Length: About 12 to 25 cm. Width: About 14 to 19 cm. Shape: Narrowly cordate. Apex: Apiculate. Base: Auriculate to cordate; lobes occasionally overlapping. Margin: Entire. Texture: Smooth, glabrous, leathery. Color: Young leaves, upper surface: 146A. Young leaves, lower surface: 146C. Mature leaves, upper surface: 147A. Mature leaves, lower surface: 146A. Petiole: Length: About 24 to 36 cm. Color: 146A. Geniculum length: About 3 to 3.5 cm. Geniculum diameter: About 5 to 7 mm. Geniculum color: 146B to 146C. Geniculum angle: About 30 to 40° C.

Inflorescence description:

*Inflorescence arrangement.*—Spathes with spadices held beyond the foliage. Flowering structures arise from leaf axils. Freely flowering; continuous flowering year-round; typically about ten inflorescences per plant.

*Inflorescence longevity.*—Inflorescences last about six weeks under winter conditions and about three months under summer conditions; persistent.

*Flowers.*—Quantity per spadix: Numerous, about 160. Shape: Rounded. Diameter: About 1 mm, maximum.

*Spathe.*—Length: About 6 to 10.5 cm. Width: About 6.5 to 12 cm. Shape: Deltoid, cordate. Apex: Apiculate to aristate. Base: Auriculate to cordate; lobes not overlapping. Margin: Entire. Texture: Leathery, glabrous, slight blistering, glossy. Color: When opening, 49B with green, 144B, veining. Opened, front surface: 49A to 55B; occasionally with green, 144B, veining. Opened, rear surface: 49D; occasionally with green, 144B veining. After senescence: 46A to green, close to 144A.

*Spadix.*—Length: About 5 to 7 cm. Diameter: About 0.6 to 1.3 cm. Shape: Columnar. Cross section: Rounded. Longitudinal axis: Very weakly recurved. Color: Apex: 13A to 13B. Mid-section: 144B to 13B. Base: 144B to 155D. After senescence: 19D.

*Scape.*—Length: About 29 to 49 cm. Aspect: Strong and erect. Color: 144A.

*Reproductive organs.*—Androecium: Pollen color: Creamy white, 159B. Gynoecium: Stigma shape: Ovoid.

Disease resistance: Under commercial conditions, plants of the new Anthurium have exhibited good tolerance to root diseases common to Anthurium.

Seed development: Seed development on plants of the new Anthurium has not been observed.

It is claimed:

1. A new and distinct cultivar of Anthurium plant named 'Wendy', as illustrated and described.

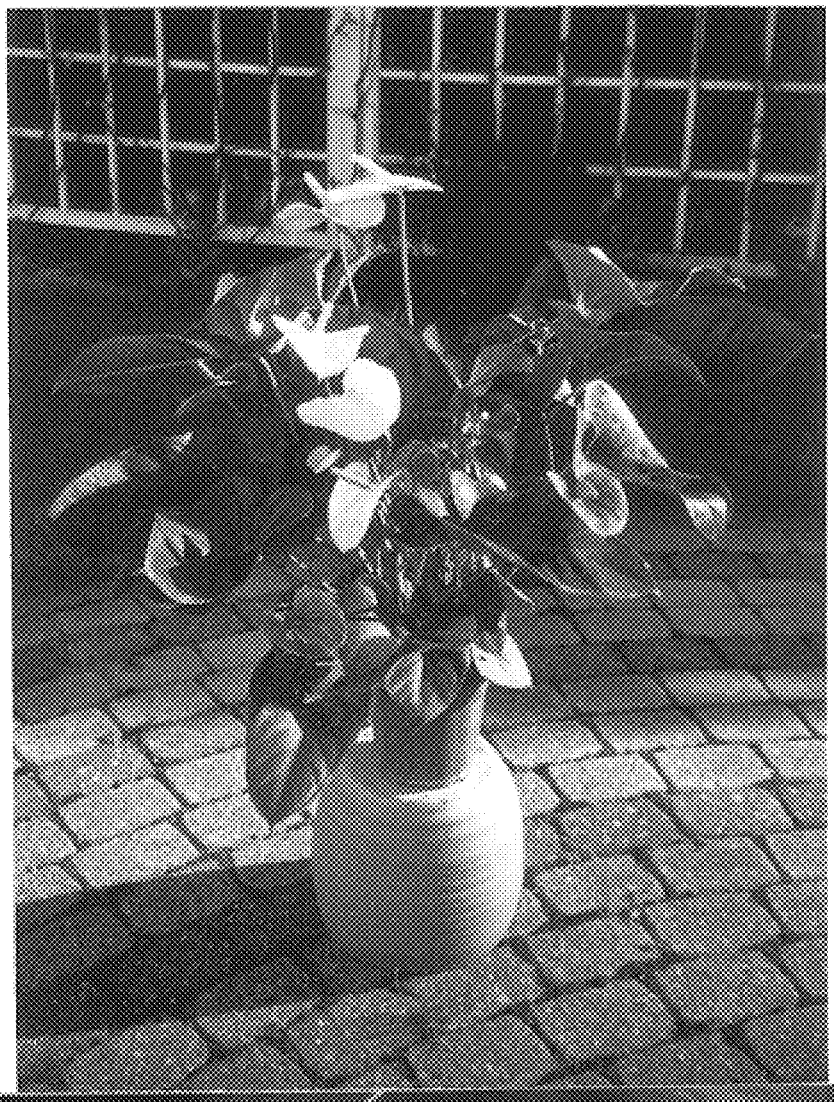
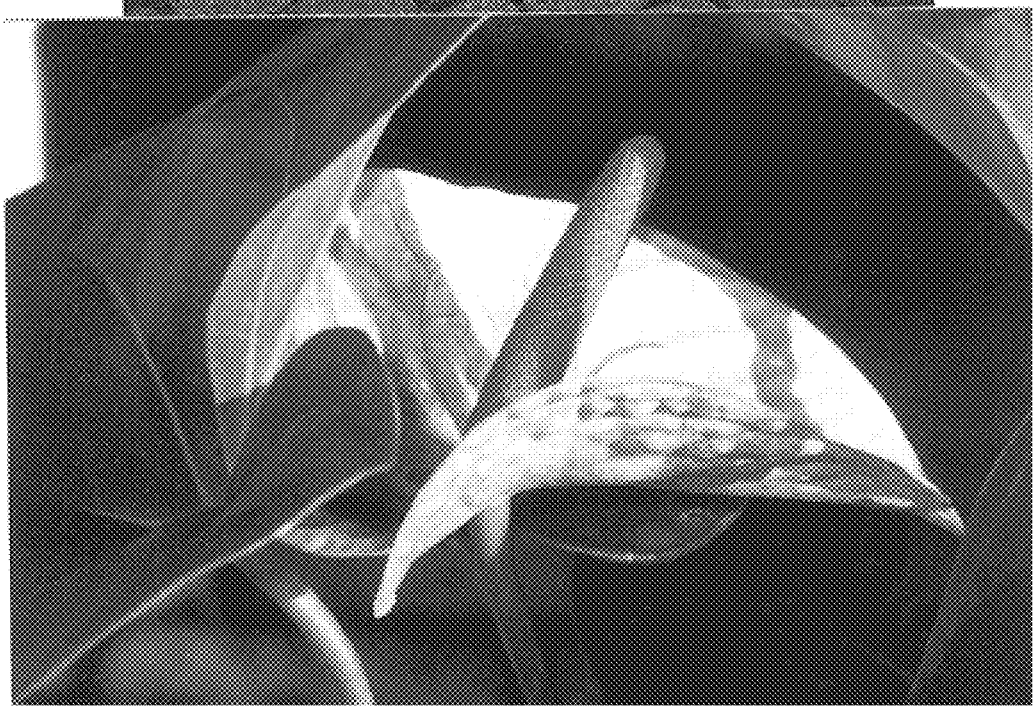

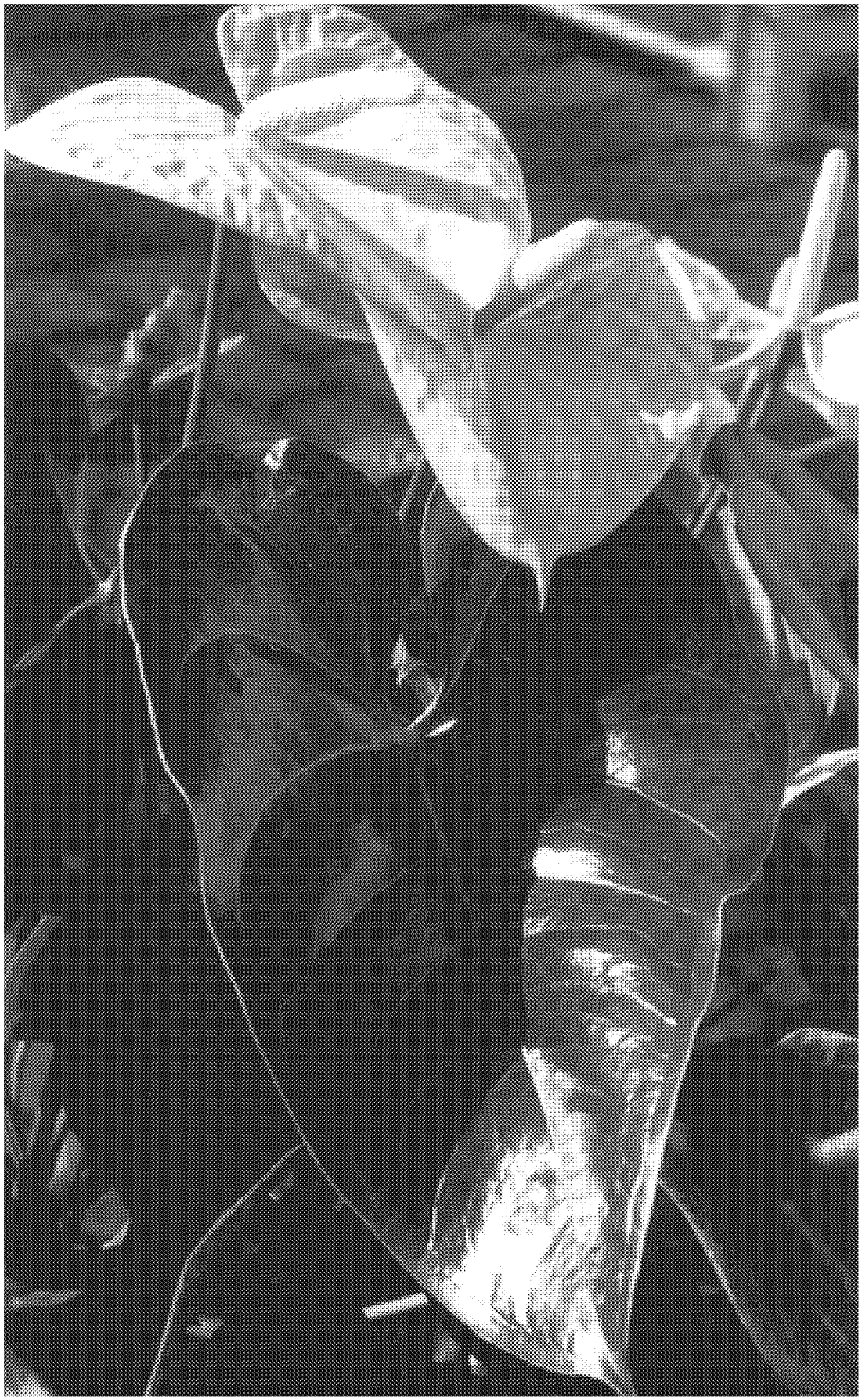

* * * * *